United States Patent
Manzer et al.

(10) Patent No.: US 6,946,563 B2
(45) Date of Patent: Sep. 20, 2005

(54) PRODUCTION OF 5-METHYL-DIHYDRO-FURAN-2-ONE FROM LEVULINIC ACID IN SUPERCRITICAL MEDIA

(75) Inventors: Leo Ernest Manzer, Lincoln Wilmington, DE (US); Keith W. Hutchenson, Lincoln University, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/462,259

(22) Filed: Jun. 16, 2003

(65) Prior Publication Data

US 2004/0254384 A1 Dec. 16, 2004

(51) Int. Cl.⁷ .............................................. C07D 307/58
(52) U.S. Cl. ..................................................... 549/326
(58) Field of Search ......................................... 549/326

(56) References Cited

U.S. PATENT DOCUMENTS

| 2,786,852 A | 3/1957 | Dunlop et al. |
| 4,420,622 A | 12/1983 | van de Moesdijk et al. |
| 5,883,266 A | 3/1999 | Elliott et al. |
| 6,617,464 B2 * | 9/2003 | Manzer ...................... 549/326 |

OTHER PUBLICATIONS

K. W. Hutchenson, Organic Chemical Reactions and Catalysis in Supercritical Fluid Media, Supercritical Fluid Technology in Materials Science and Engineering, Y. P. Sun (ed.) Marcel Dekker: New York, 2002, pp. 87–187.
PCT/US2004/01968, International Search Report Dated Dec. 17, 2004.

* cited by examiner

*Primary Examiner*—Bernard Dentz

(57) ABSTRACT

This invention relates to a process for producing 5-methyl-dihydro-furan-2-one from levulinic acid in presence of a supercritical fluid, and in presence of optionally-supported metal catalyst.

15 Claims, No Drawings

PRODUCTION OF 5-METHYL-DIHYDRO-FURAN-2-ONE FROM LEVULINIC ACID IN SUPERCRITICAL MEDIA

FIELD OF INVENTION

This invention relates to a process for producing 5-methyl-dihydro-furan-2-one from levulinic acid in presence of a supercritical fluid, and in presence of optionally-supported metal catalyst.

TECHNICAL BACKGROUND

Levulinic acid is a well-known product of hexose acid hydrolysis, and is inexpensively obtained from cellulose feedstocks. Consequently, it is an attractive starting material in producing useful 5-carbon compounds, such as methyltetrahydrofuran and derivatives. 5-methyl-dihydro-furan-2-one, also known as gamma-valerolactone, can be produced from levulinic acid as shown below.

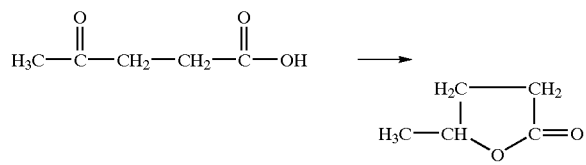

U.S. Pat. No. 5,883,266 discloses the use of a bifunctional catalyst having a first function of hydrogenating and a second function of ring opening to prepare a variety of products from levulinic acid including 5-methyl-dihydro-furan-2-one.

U.S. Pat. No. 2,786,852 disclosed production of 5-methyl-dihydro-furan-2-one from levulinic acid using a reduced copper oxide catalyst.

U.S. Pat. No. 4,420,622 discloses preparation of 5-alkyl-butyrolactones from levulinic esters using metal catalysts.

The present method represents an advance in the art by offering a process that exploits several advantages of using a supercritical fluid (SCF) as the reaction solvent. SCFs are attractive media for conducting chemical transformations, primarily because the solvent and transport properties of a single solution can be varied appreciably and continuously with relatively minor changes in temperature or pressure. The density variation in a SCF also influences the chemical potential of solutes and thus reaction rates and equilibrium constants. Thus, the solvent environment can be optimized for a specific reaction application by tuning the various density-dependent fluid properties. For a discussion of advantages and applications of supercritical fluid media for chemistry and catalysis, see Hutchenson, K. W., "Organic Chemical Reactions and Catalysis in Supercritical Fluid Media," in *Supercritical Fluid Technology in Materials Science and Engineering*, Y. -P. Sun (ed.), Marcel Dekker: New York (2002), pp. 87–187. SCF-mediated reaction processes have the potential for utilizing a reaction medium that exhibits improved safety, health, and environmental impact relative to typical organic solvents. Carbon dioxide and other SCF solvents are generally considered environmentally benign, nontoxic, nonflammable, and inexpensive, useful solvent at relatively moderate temperatures.

SUMMARY OF THE INVENTION

This invention relates to a process for preparing 5-methyl-dihydro-furan-2-one comprising heating levulinic acid in a supercritical fluid medium in the presence of hydrogen and a catalytic amount of an optionally supported catalytic metal.

DETAILED DESCRIPTION OF THE INVENTION

The invention is directed to a process for the preparation of 5-methyl-dihydro-furan-2-one, also known as gamma-valerolactone, from levulinic acid in the presence of a metal catalyst, in a supercritical medium.

A fluid is in the supercritical fluid state when the system temperature and pressure exceed the corresponding critical point values defined by the critical temperature ($T_c$) and pressure ($P_c$) Most useful applications of SCFs which take advantage of the unusual physical properties in this region occur in the range of reduced properties of $T_R$ (=$T/T_c$) ≈1.0–1.1 and $P_R$ (=$P/P_c$)≈1.0–2.0. However, many of the potential benefits afforded by a SCF solvent can be realized at conditions slightly sub-critical in temperature or pressure.

One of the primary advantages of SCF reaction media is that the density can be varied continuously from liquid-like to gas-like values by either varying the temperature or pressure, and to a first approximation, the solvent strength of the SCF media can be related to this continuously-variable solution density. The various density-dependent physical properties (e.g., solvent polarity) also exhibit similar continuous variation in this region. In general, a SCF in the vicinity of its critical point has a liquid-like density and solvent strength, but exhibits transport properties (mass, momentum, and thermal diffusivities) that are intermediate to those of gases and liquids.

Since gaseous reactants are completely miscible with SCFs, their concentrations in SCF reaction media are significantly higher than are obtainable in conventional liquid solvents, even at appreciable pressures. These higher reactant concentrations in SCF media combined with increased component diffusivities and relatively low system viscosities can result in mass transfer rates that are appreciably higher than in liquid solvents. This can potentially shift a chemical reaction rate from mass transfer control to kinetic control in the reactor. The solubility of gaseous reactants in liquid solvents can also be enhanced by a volume expansion of the solvent with a dense supercritical fluid, which likewise results in increased mass transfer rates. Improved mass transport can also result in enhanced removal of residual solvents. In addition to typical factors such as chemical inertness, cost, toxicity, etc., the critical temperature must be considered when selecting a potential solvent for conducting chemical transformations in the SCF regime. For practical applications, thermal and catalytic chemical reactions can only be conducted in a relatively narrow temperature range. Lower temperatures result in unacceptable reaction rates, and higher temperatures can result in significant selectivity and yield losses as well as catalyst deactivation. To obtain practical solvent densities and the corresponding density-dependent properties, this temperature optimization must be balanced against a general desire to operate in the vicinity of the mixture critical point of the reaction system to fully exploit the potential advantages afforded by SCF operation. The phase behavior of the reaction mixture, which is strongly influenced by the solvent critical temperature, is fundamentally important in defining this operating window, so one must select a solvent to provide the desired phase behavior. The phase behavior of SCF systems can also be manipulated to control the number and composition of coexisting phases, thus controlling both reaction effects as well as the separation of products or homogeneous catalysts from the reaction mixture. Finally, the addition of cosolvents can be effectively utilized to exploit specific solute interactions such as enhancing solute solubilities and influencing reaction selectivities, and equilibria.

By "supercritical fluid" herein is meant a state of matter for a substance or a mixture of substances that exists above the critical temperature and critical pressure of the substance or mixture. For pure substances, the critical temperature and pressure are the highest at which vapor and liquid phases can coexist. Above the critical temperature, a liquid does not form for a pure substance, regardless of the applied pressure. Similarly, the critical pressure and critical molar volume are defined at this critical temperature corresponding to the state at which the vapor and liquid phases merge. Similarly, although more complex for multicomponent mixtures, the mixture critical state is identified as the condition at which the properties of coexisting vapor and liquid phases become indistinguishable. In practice, a number of desirable properties characteristic of the SCF state are realized in the expanded liquid region that exists at temperatures and pressures slightly below this critical point. Hence, for the purposes of this document, the term "supercritical fluid" also includes such "near-critical fluids," as defined below. For a discussion of supercritical fluids, see *Kirk-Othmer Encycl. of Chem. Technology*, 4$^{th}$ Ed., Vol. 23, pg. 452–477.

Importantly, the subject substance will begin to manifest many of the physical traits of a supercritical fluid before conditions actually cause the change of state of matter. This phenomenon is analogous to other changes in states of matter, such as when water is heated to the boiling point. Just prior to the water reaching the temperature at which it boils, it behaves similarly to the steam it will become in terms of molecular kinetics, energy, and, temperature. Just prior to a liquid or gas becoming a supercritical fluid, it also begins to manifest some of the physical properties and attributes, such as density, viscosity, diffusivity and solubility, of the supercritical fluid it will become. The mixture is termed a "near-critical fluid" when the fluid is either at or below the critical temperature and the properties begin to approach those of a supercritical fluid. For the purposes of this discussion "near-critical fluid" includes those conditions where the fluid is at temperatures from about 75% of the critical temperature to about 100% of the critical temperature, and pressures from about 25% of the critical pressure to about 100% of the critical pressure.

Supercritical fluids exhibit properties intermediate between those of gases and liquids. A key feature of a SCF is that the fluid density can be varied continuously from liquid-like to gas-like densities by varying either the temperature or pressure, or a combination thereof. Various density-dependent physical properties likewise exhibit similar continuous variation in this region. Some of these properties include, but are not limited to, solvent strength (as evidenced by the solubilities of various substances in the SCF media), polarity, viscosity, diffusivity, heat capacity, thermal conductivity, isothermal compressibility, expandability, contractibility, fluidity, and molecular packing. The density variation in a SCF also influences the chemical potential of solutes and hence, reaction rates and equilibrium constants. Thus, the solvent environment in a SCF media can be optimized for a specific reaction application by tuning the various density-dependent fluid properties.

Any suitable SCF may be used in the processes of the invention, including, but not limited to, carbon dioxide, nitrous oxide, sulfur hexafluoride, fluoromethane, trifluoromethane, tetrafluromethane, ethane, propane, propanol, isopropanol, butane, butanol, isobutane, pentane, hexane, cyclohexane, water, and mixtures thereof, provided that it is inert to all reagents and products. Preferred is where the supercritical fluid is carbon dioxide or a $C_1$–$C_6$ alkane, optionally substituted with Cl, F or Br. More preferred is where the supercritical fluid is carbon dioxide, trifluoromethane, pentane or propane.

In the context of this disclosure, a number of terms and abbreviations shall be utilized. The following abbreviations and definitions are provided:

Abbreviations
GVL gamma-valerolactone
GC Gas chromatography
i.d. internal diameter
LA Levulinic acid
LA Conv. Levulinic Acid Conversion
GVL Sel. Selectivity to 5-methyl-dihydro-furan-2-one
MW Number average molecular weight
MS Mass spectroscopy
NMR Nuclear magnetic resonance
SCF Supercritical fluid
Definitions By 5-methyl-dihydro-furan-2-one or gamma-valerolactone is meant the compound represented by Formula I.

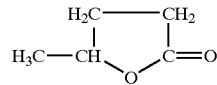

FORMULA I

By levulinic acid is meant the compound represented by Formula II.

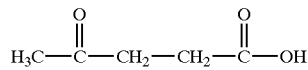

FORMULA II

Catalyst

The reaction of this invention is effected in the presence of a catalytic metal. The principal component of the catalyst is selected from the group consisting of palladium, ruthenium, rhenium, rhodium, iridium, platinum, nickel, cobalt, copper, iron, osmium, compounds thereof, and combinations thereof.

The catalytic metal can optionally be supported on a catalyst support. The catalyst support can be in the form of powder, granules, pellets, or the like. A supported catalyst is one in which the active catalyst agent is deposited on a support material by a number of methods, such as spraying, soaking or physical mixing, followed by drying, calcination, and if necessary, activation through methods such as reduction or oxidation. Commonly used techniques for treatment of supports with metal catalysts can be found in B. C. Gates, Heterogeneous Catalysis, Vol. 2, pp. 1–29, Ed. B. L. Shapiro, Texas A & M University Press, College Station, Tex., 1984. Materials frequently used as support are porous solids with high total surface areas (external and internal) which can provide high concentrations of active sites per unit weight of catalyst. The catalyst support may enhance the function of the catalyst agent.

The catalyst support useful herein can be any solid, and optionally an inert substance. A preferred support material of the invention is selected from the group consisting of carbon, alumina, silica, silica-alumina, silica-titania, titania, titania-alumina, barium sulfate, calcium carbonate, strontium carbonate, various zeolites compounds thereof and combinations thereof. Supported catalytic metals can also have supporting materials made from one or more compounds. More preferred supports are alumina, titania and carbon. Further preferred supports are carbons with a surface area greater than 100 $m^2/g$. A further preferred support is carbon with a surface area greater than 200 $m^2/g$. Most preferred supports are "oxidatively stable carbons."

"Oxidatively stable carbon" is hereby defined as carbon that exhibits substantial weight stability when heated in air. Such carbons are described further in International Publication WO 97/30932.

The most preferred carbons employed as support materials for the process of this invention lose less than 20% of their weight under the WVC Temperature Test. This sequence of time and temperature conditions for evaluating the effect of heating carbon samples in air is defined herein as the "WVC Temperature Test." The WVC Temperature Test may be run using thermal gravimetric analysis (TGA). More particularly, the WVC test comprises the steps of heating the carbons in air at 125° C. for 30 min, followed by heating at 200° C. for 30 min, followed by heating at 300° C. for 30 min, followed by heating at 350° C. for 45 min, followed by heating at 400° C. for 45 min, followed by heating at 450° C. for 45 min and finally followed by heating at 500° C. for 30 min.

Carbons which when subjected to the WVC Temperature Test lose about 20% of their weight, or less, are considered to be advantageously oxidatively stable. Carbon from any of the following sources are useful for the process of this invention: wood, peat, coal, coconut shells, bones, lignite, petroleum-based residues and sugar.

Commercially available carbons which may be used in this invention include those sold under the following trademarks: Barneby & Sutcliffe™, Darco™, Nuchar™, Columbia JXN™, Columbia LCK™, Calgon PCB™, Calgon BPL™, Westvaco™, Norit™ and Barnaby Cheny NB™. The carbon can also be commercially available carbon such as Calsicat C, Sibunit C, or Calgon C (commercially available under the registered trademark Centaur(R)).

The catalysts of the present invention may optionally comprise catalyst additives and promoters that will enhance the efficiency of the catalyst. Optionally, the catalyst can include one or more promoters. Preferably the promoter is also a metal, where the promoter is present in less than about 50 weight percent compared to the catalytic metal. Particularly useful in the present invention are promoters with principal component from gold, sodium, potassium, cesium, barium, rhenium, iron, and chromium, tin, zinc, copper, silver, and combinations thereof. Other promoters that can be used have the prinicipal component from the Group 1 and Group 2 elements of the Periodic Table. Use of these materials are common and well known in the art (see for example, Kirk-Othmer Encyclopedia of Chemical Technology, Howe-Grant Ed., Vol. 5, pp 326–346, (1993), John Wiley & Sons, New York and Ullmann's Encyclopedia of Industrial Chemistry, Vol. A5, Gerhartz et al., Eds., pp. 337–346, (1986), VCH Publishers, New York, both herein incorporated by reference.) The relative percentages of the catalyst promoter may vary. Useful amounts of promoter will be from about 0.01% to about 50% by weight of catalyst.

Each catalyst individually has both a hydrogenation and a ring-closing function; that is, the reaction proceeds in one step and produces little or none of the pentyl alcohols such as pentanediol.

A catalyst which is not supported on a catalyst support material is an unsupported catalyst. An unsupported catalyst may be platinum black or a Raney® catalyst. Raney® catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney® catalysts include nickel, copper, cobalt, iron, rhodium, ruthenium, rhenium, osmium, iridium, platinum, palladium, compounds thereof and combinations thereof.

Promoter metals may also be added to the base Raney® metals (available from W. R. Grace & Co., Columbia Md.) listed above to affect selectivity and/or activity of the Raney® catalyst. Promoter metals for Raney® catalysts may be selected from transition metals from Groups 3 through Group 8, and Group 11 and Group 12 of the Periodic Table of the Elements. Examples of promoter metals for the Raney® based catalytic metal include chromium, molybdenum, platinum, rhodium, ruthenium, osmium, and palladium, typically at about 2% by weight of the total metal.

In the processes of the invention, the preferred catalytic metal content range of the supported catalyst is from about 0.1% to about 20% of the supported catalyst based on catalyst weight plus the support weight. A more preferred catalytic metal content range is from about 1% to about 10% of the supported catalyst. A further preferred catalytic metal content range is from about 1% to about 5% of the supported catalyst.

Combinations of catalytic metal and support system may include any one of the metals referred to herein with any of the supports referred to herein. Preferred combinations of catalytic metal and support system include palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, and rhenium on alumina.

Most preferred combinations of catalytic metal and support systems for the processes of this invention include ruthenium on carbon, ruthenium on alumina, ruthenium on silica, ruthenium on titania, ruthenium on silica-alumina, ruthenium on silica-titania, ruthenium on titania-alumina, ruthenium on barium sulfate, ruthenium on calcium carbonate, ruthenium on strontium carbonate, ruthenium on various zeolites, ruthenium on compounds thereof and ruthenium on combinations thereof. A further preferred combination of catalytic metal and support systems for the processes of this invention includes ruthenium on oxidatively stable carbons.

Further preferred combinations of catalytic metal and support system include palladium on carbon, palladium on alumina, palladium on titania, platinum on carbon, platinum on alumina, rhodium on carbon, rhodium on alumina, ruthenium on carbon and ruthenium on alumina.

The temperature of the reaction can range from about 70° C. to about 400° C., with a preferred range of about 100° C. to about 350° C. A more preferred range is about 125° C. to about 250° C. Pressure ranges are those required to achieve supercritical or near-critical state under the reaction conditions present. The pressure of the reaction can range from about 5 to about 60 MPa, with a preferred range of about 15 to about 40 MPa. Contact time can be selected to achieve the desired yields and selectivities, which can also be enhanced by additional contact with the catalyst.

Reactors suitable for processes of the instant invention include continuous stirred tank reactors (CSTR), batch stirred tank reactors, (stirred batch reactors), semi-batch stirred tank reactors, tubular reactors, fixed bed reactors, and trickle bed reactors. The process can be run in either batch or continuous mode as described in H. Scott Fogler, *Elements of Chemical Reaction Engineering,* 2nd Edition, Prentice-Hall Inc, California, 1992. The process can also be run in either a single homogeneous phase over the solid catalyst, or the reactants and SCF may be in two different phases over the solid catalyst.

Separation and/or purification of the product may be performed by any process known in the art. One particularly suitable method is by density reduction via pressure or temperature drop.

The following Examples further illustrate the invention.

EXPERIMENTAL

Materials and Methods

The following catalyst supports are used in the following examples. Oxidatively stable carbon catalyst supports were tested for weight stability via thermogravimetric analysis according to the WVC Temperature Test. Support systems available from other commercially available sources can also be used for the purposes of this invention.

| Support | Source |
| --- | --- |
| Sibunit Carbon | Boreskov Inst. of Catalysis, Novosibirsk, Russia |
| Silica grade 55 | W. R. Grace & Co., Columbia, MD |
| Calsicat Carbon | Engelhard Corp., E. Windsor, CT |
| Alumina | Harshaw Chemical Co., Cleveland, OH |
| Titania | Engelhard Corp. (E. Windsor, CT) |

EXAMPLES

The catalysts were obtained commercially or prepared by impregnating the catalyst support by incipient wetness with a metal salt. The precursors used were $NiCl_2 \cdot 6H_2O$ (Alfa Aesar, Ward Hill, Mass.), $Re_2O_7$ (Alfa), $PdCl_2$ (Alfa), $RuCl_3 \cdot xH_2O$ (Aldrich, Milwaukee, Wis.), $H_2PtCl_6$ (Johnson Matthey, Ward Hill, Mass.), 5% Rh using $RhCl_3 \cdot xH_2O$ (Alfa), $Re_2O_7$ (Alfa) and $IrCl_3 \cdot 3H_2O$ (Johnson Matthey). The samples were dried and reduced at 400° C. in hydrogen atmosphere for 2 hours.

Hydrogenation of Levulinic Acid to 5-methyl-dihydro-furan-2-one in the Presence of Supercritical Fluid

Example 1

Levulinic acid (0.146 moles) and 0.851 g of a 5% $Ru/Al_2O_3$ catalyst (Engelhard ESCAT 44) were charged to a 50 mL stirred batch autoclave reactor. The vessel was heated to 150° C. and charged with 105 bar (10.5 MPa) pressure of $CO_2$ (approximately 0.137 moles). The reactor was then charged to a total pressure of 250 bar (25.0 MPa) with hydrogen, approximately corresponding to the stoichiometric quantity to hydrogenate the levulinic acid. The reactor temperature was maintained at 150° C. for 2 hours, and the total pressure was maintained at 250 bar (25.0 MPa) by addition of $CO_2$ to match the consumption of hydrogen. The reactor was then thermally quenched and vented. Product analysis by gas chromatography (GC-FID) showed 99.5% conversion of the levulinic acid with 99.7% selectivity to 5-methyl-dihydro-furan-2-one.

Example 2

Levulinic acid (0.147 moles) and 0.851 g of a 5% $Ru/Al_2O_3$ catalyst (Engelhard ESCAT 44) were charged to a 50 mL stirred batch autoclave reactor. The vessel was heated to 150° C. and charged with 75 bar (7.5 MPa) pressure of propane (approximately 0.153 moles). The reactor was then charged to a total pressure of 250 bar (25.0 MPa) with hydrogen, approximately corresponding to 5% excess of the stoichiometric quantity to hydrogenate the levulinic acid. The reactor temperature was maintained at 151° C. for 1.5 hours, and the total pressure was maintained at 250 bar (25.0 MPa) by addition of propane to match the consumption of hydrogen. The reactor was then thermally quenched and vented. Product analysis by gas chromatography (GC-FID) showed 14.9% conversion of the levulinic acid with 93.4% selectivity to 5-methyl-dihydro-furan-2-one.

Example 3

Levulinic acid (0.150 moles) and 0.852 g of a 1% Ru+6% Re/Calsicat Carbon catalyst were charged to a 50 mL stirred batch autoclave reactor. The vessel was heated to 150° C. and charged with 99 bar (9.9 MPa) pressure of $CO_2$ (approximately 0.128 moles). The reactor was then charged to a total pressure of 250 bar (25.0 MPa) with hydrogen, approximately corresponding to 5% excess of the stoichiometric quantity to hydrogenate the levulinic acid. The reactor temperature was maintained at 150° C. for 2 hours, and the total pressure was maintained at 250 bar (25.0 MPa) by addition of $CO_2$ to match the consumption of hydrogen. The reactor was then thermally quenched and vented. Product analysis by gas chromatography (GC-FID) showed 16.5% conversion of the levulinic acid with 96.1% selectivity to 5-methyl-dihydro-furan-2-one.

Continuous Flow Reactor Hydrogenation Examples

Examples 4–9

A 77 wt % solution of levulinic acid in dioxane with 4 wt % n-nonane as an internal standard was combined with carbon dioxide and hydrogen, and the combined solution was fed to a continuous fixed bed reactor (6.2 mm i.d.×260 mm long) charged with catalyst. The catalysts were prepared by impregnating the various catalyst supports by incipient wetness with $RuCl_3 \cdot xH_2O$ metal salt. The catalyst samples were dried and reduced at 400° C. in $H_2$ for 2 hours prior to use in the hydrogenation reaction. The reactor effluent was cooled, vented, and collected for product analysis. The products were analyzed by gas chromatography (GC-FID) using n-nonane as an internal standard. Reaction conditions and results of product analysis are shown in Table 1 below.

Continuous Flow Reactor Hydrogenation Examples

Examples 10–18

A 79 wt % solution of levulinic acid in dioxane was combined with carbon dioxide and hydrogen, and the combined solution was fed to a continuous fixed bed reactor (6.2 mm i.d.×260 mm long) charged with commercially-available catalysts. The reactor effluent was cooled, vented, and collected for product analysis. The products were analyzed by gas chromatography (GC-FID). Reaction conditions and results of product analysis are shown in Table 1 below.

Continuous Flow Reactor Hydrogenation Examples

Examples 19–30

A 70 wt % solution of levulinic acid in dioxane was combined with carbon dioxide and hydrogen, and the combined solution was fed to a continuous fixed bed reactor (either 6.2 mm i.d.×260 mm long, or 7.7 mm i.d.×260 mm long) charged with commercially-available catalysts. The reactor effluent was cooled, vented, and collected for product analysis. The products were analyzed by gas chromatography (GC-FID). Reaction conditions and results of product analysis are shown in Table 1 below.

Examples 31–41

In additional examples, levulinic acid, or a solution of levulinic acid and inert organic solvent, is combined with carbon dioxide and hydrogen, and the combined feed flows to a continuous fixed bed reactor charged with catalyst. The catalysts are either obtained commercially or are prepared by impregnating the various catalyst supports by incipient wetness with a metal salt. The catalyst precursors used are $PdCl_2$, $RuCl_3 \cdot xH_2O$, $H_2PtCl_6$, and $IrCl_2 \cdot 3H_2O$. The catalyst samples are dried and reduced at 400° C. in $H_2$ for 2 hours prior to use in the hydrogenation reaction. The reactor effluent is cooled, vented and collected for product analysis. The products are analyzed by gas chromatography (GC-FID) using n-nonane as an internal standard. Reaction conditions and results of product analysis are shown in Table 2 below.

TABLE 1

| Ex. | Catalyst | Cat. Load (g) | Temp. (° C.) | Pressure (MPa) | LA* (mol/min) | $H_2$:LA (mol/mol) | $CO_2$ mol/min | LA Conv. (%)** | GVL Sel. (%) |
|---|---|---|---|---|---|---|---|---|---|
| 4 | 5% Ru/Sibunit C | 1.25 | 150 | 25.0 | 0.00179 | 1.25 | 0.01070 | 13.9 | 98.4 |
| 5 | 5% Ru/Sibunit C | 1.25 | 174 | 25.0 | 0.00091 | 3.0 | 0.01202 | 42.1 | 99.9 |
| 6 | 5% Ru/$Al_2O_3$ | 1.00 | 175 | 25.0 | 0.00072 | 3.0 | 0.00773 | 31.5 | 99.7 |
| 7 | 5% Ru/$Al_2O_3$ | 1.00 | 175 | 20.0 | 0.00072 | 3.0 | 0.00546 | 29.4 | 98.9 |
| 8 | 5% Ru/$Al_2O_3$ | 1.00 | 175 | 30.0 | 0.00072 | 3.0 | 0.00971 | 13.9 | 97.0 |
| 9 | 5% Ru/$Al_2O_3$ | 1.00 | 199 | 27.9 | 0.00072 | 3.0 | 0.00773 | 23.1 | 98.9 |
| 10 | 5% Pt/$SiO_2$ | 1.00 | 176 | 20.1 | 0.00072 | 1.0 | 0.00858 | 5.1 | 80.0 |
| 11 | 1% Ru/$SiO_2$ | 1.00 | 176 | 20.2 | 0.00044 | 1.0 | 0.00910 | 10.6 | 99.8 |
| 12 | 1% Ru/$SiO_2$ | 1.00 | 200 | 20.3 | 0.00044 | 1.0 | 0.00808 | 13.1 | 99.8 |
| 13 | 1% Ru/$SiO_2$ | 1.00 | 200 | 20.3 | 0.00044 | 2.0 | 0.00764 | 16.3 | 99.8 |
| 14 | 1% Ru/$SiO_2$ | 1.00 | 200 | 25.0 | 0.00044 | 2.0 | 0.00995 | 33.2 | 99.9 |
| 15 | 5% Ru/$Al_2O_3$ | 1.61 | 200 | 20.2 | 0.00024 | 2.0 | 0.00274 | 21.7 | 98.6 |
| 16 | 5% Ru/$Al_2O_3$ | 1.61 | 200 | 25.1 | 0.00024 | 2.0 | 0.00201 | 17.4 | 99.6 |
| 17 | 5% Ru/Sibunit C | 2.02 | 201 | 20.1 | 0.00022 | 2.0 | 0.00524 | 73.6 | 99.5 |
| 18 | 1% Ru/$Al_2O_3$ | 2.98 | 201 | 20.0 | 0.00032 | 1.25 | 0.00795 | 75.8 | 99.3 |
| 19 | 1% Ru/$Al_2O_3$ | 5.18 | 201 | 20.0 | 0.00038 | 1.0 | 0.0102 | 98.7 | 100. |
| 20 | 1% Ru/$SiO_2$ | 2.43 | 200 | 20.0 | 0.00017 | 1.0 | 0.00972 | 26.9 | 99.2 |
| 21 | 5% Ru/$Al_2O_3$ | 4.68 | 201 | 20.1 | 0.00034 | 1.0 | 0.00975 | 97.8 | 99.2 |
| 22 | 1% Ru/$Al_2O_3$ | 3.18 | 201 | 20.1 | 0.00022 | 1.0 | 0.00641 | 62.0 | 96.8 |
| 23 | 1% Ru/$Al_2O_3$ | 7.12 | 201 | 20.1 | 0.00038 | 1.0 | 0.0109 | 91.8 | 99.8 |
| 24 | 1% Ru/$Al_2O_3$ | 7.07 | 125 | 20.0 | 0.00037 | 1.2 | 0.0106 | 97.3 | 99.9 |
| 25 | 1% Ru/$Al_2O_3$ | 7.02 | 151 | 23.2 | 0.00037 | 1.2 | 0.0106 | 99.6 | 100. |
| 26 | 1% Ru/$Al_2O_3$ | 4.55 | 141 | 21.8 | 0.00030 | 1.2 | 0.00849 | 98.3 | 100. |
| 27 | 3.5% Ru/$TiO_2$ | 3.90 | 140 | 21.9 | 0.00030 | 1.2 | 0.00849 | 70.8 | 99.7 |
| 28 | 5% Ru/$Al_2O_3$ | 4.50 | 141 | 21.8 | 0.00030 | 1.2 | 0.00849 | 31.1 | 100. |
| 29 | 5% Rh/Calsicat C | 2.95 | 141 | 24.7 | 0.00030 | 1.2 | 0.00849 | 98.9 | 100. |
| 30 | 5% Ir/Sibunit C | 3.04 | 141 | 25.0 | 0.00030 | 1.2 | 0.00849 | 43.0 | 99.3 |

TABLE 2

| Ex. | Catalyst | Cat. Load (g) | Temp. (° C.) | Pressure (MPa) | LA (mol/min) | $H_2$:LA (mol/mol) | $CO_2$ (mol/min) | LA Conv. (%) | GVL Sel. (%) |
|---|---|---|---|---|---|---|---|---|---|
| 31 | 5% Ru/Calsicat C | 1.00 | 140 | 20.0 | 0.00030 | 1.2 | 0.00850 | >30 | >90 |
| 32 | 5% Ir/$Al_2O_3$ | 1.00 | 140 | 20.0 | 0.00030 | 1.2 | 0.00850 | >30 | >85 |
| 33 | 5% Ir/Calsicat C | 1.00 | 140 | 20.0 | 0.00030 | 1.2 | 0.00850 | >30 | >85 |
| 34 | 5% Ir/$SiO_2$ | 1.00 | 140 | 20.0 | 0.00030 | 1.2 | 0.00850 | >20 | >75 |

TABLE 2-continued

| Ex. | Catalyst | Cat. Load (g) | Temp. (° C.) | Pressure (MPa) | LA (mol/ min) | H$_2$:LA (mol/ mol) | CO$_2$ (mol/ min) | LA Conv. (%) | GVL Sel. (%) |
|---|---|---|---|---|---|---|---|---|---|
| 35 | 5% Pt/ Al$_2$O$_3$ | 1.00 | 140 | 20.0 | 0.00030 | 1.2 | 0.00850 | >20 | >80 |
| 36 | 5% Pt/ Sibunit C | 1.00 | 140 | 20.0 | 0.00030 | 1.2 | 0.00850 | >20 | >80 |
| 37 | 5% Pt/ Calsicat C | 1.00 | 140 | 20.0 | 0.00030 | 1.2 | 0.00850 | >20 | >80 |
| 38 | 5% Pd/ Al$_2$O$_3$ | 1.00 | 140 | 20.0 | 0.00030 | 1.2 | 0.00850 | >20 | >80 |
| 39 | 5% Pd/ Sibunit C | 1.00 | 140 | 20.0 | 0.00030 | 1.2 | 0.00850 | >20 | >80 |
| 40 | 5% Pd/ Calsicat C | 1.00 | 140 | 20.0 | 0.00030 | 1.2 | 0.00850 | >20 | >80 |
| 41 | 5% Pd/ SiO$_2$ | 1.00 | 140 | 20.0 | 0.00030 | 1.2 | 0.00850 | >15 | >70 |

What is claimed is:

1. A process for preparing 5-methyl-dihydro-furan-2-one comprising forming a reaction mixture comprising levulinic acid and a solvent in the presence of hydrogen and a catalytic amount of an optionally supported catalytic metal, and subjecting the reaction mixture to a temperature and pressure sufficient to cause the reaction mixture to exist as a supercritical or near-critical fluid phase.

2. The process as recited in claim 1, wherein said solvent is selected from a group consisting carbon dioxide, nitrous oxide, sulfur hexafluoride, fluoromethane, trifluoromethane, tetrafluromethane, propanol, isopropanol butanol, isobutane, cyclohexane, water, C1–C6 alkane, C1–C6 alkane substituted with Cl, C1–C6 alkane substituted F, C1–C6 alkane substituted with Br, and mixtures thereof.

3. The process as recited in claim 2, wherein said catalytic metal support is selected from a group consisting of silica, titania, zirconia, alumina, carbon, zeolite, silica-alumina, silica-titania, titania-alumina, barium sulfate, calcium carbonate, strontium carbonate, compounds thereof and combinations thereof.

4. The process as recited in claim 3, wherein said catalytic metal is selected from a group consisting of palladium, ruthenium, rhenium, rhodium, iridium, platinum, nickel, cobalt, copper, iron, osmium, compounds thereof, and combinations thereof.

5. The process as recited in claim 3, wherein said catalytic metal is ruthenium.

6. The process as recited in claim 4, wherein said support is oxidatively stable carbon or alumina.

7. The process as recited in claim 3, wherein said catalytic metal is a Raney® catalytic metal.

8. The process as recited in claim 1, wherein said process is performed at a temperature from about 70° C. to about 400°C.

9. The process as recited in claim 1, wherein said process is performed at a temperature of about 125° C. to about 250°C.

10. The process as recited in claim 1, wherein said process is performed at a pressure of about 5.0 MPa to about 60.0 MPa.

11. The process as recited in claim 1, wherein said process is performed at a pressure of about 15.0 MPa to about 40.0 MPa.

12. The process as recited in claim 11, wherein said catalytic metal is promoted with at least one promoter.

13. The process as recited in claim 11, wherein said promoter is a metal.

14. The process as recited in claim 12, wherein the promoter is selected from a group consisting of gold, sodium, potassium, cesium, barium, rhenium, iron, chromium, tin, zinc, copper, silver, Group 1 elements of the Periodic Table, Group 2 elements of the Periodic Table, and combinations thereof.

15. A process as recited in claim 1, wherein said solvent is carbon dioxide, said catalytic metal is ruthenium, said support is oxidatively stable carbon or alumina, the process is performed at a pressure in the range of from about 18.0 MPa to about 35.0 MPa, the temperature of reaction is of from about 125° C. to about 250°C., wherein said catalytic metal is promoted with a metal promoter selected from a group consisting of gold, sodium, potassium, cesium, barium, rhenium, iron, chromium, tin, zinc, copper, silver, Group 1 elements of the Periodic Table, Group 2 elements of the Periodic Table, and combinations thereof.

* * * * *